United States Patent
Bose et al.

(10) Patent No.: US 9,943,607 B2
(45) Date of Patent: *Apr. 17, 2018

(54) BETA-GLUCAN COMPOUNDS, COMPOSITIONS, AND METHODS

(75) Inventors: Nandita Bose, Plymouth, MN (US); Anissa S. H. Chan, Arden Hills, MN (US); Michael E. Danielson, St. Paul, MN (US); Mary A. Antonysamy, Woodbury, MN (US); John P. Vasilakos, Woodbury, MN (US); Keith B. Gorden, Woodbury, MN (US); Steven M. Leonardo, Eagan, MN (US); William J. Grossman, Third Lake, IL (US)

(73) Assignee: Biothera, Inc., Eagan, MN (US)

( * ) Notice: Subject to any disclaimer, the term of this patent is extended or adjusted under 35 U.S.C. 154(b) by 362 days.

This patent is subject to a terminal disclaimer.

(21) Appl. No.: 14/116,550

(22) PCT Filed: May 9, 2012

(86) PCT No.: PCT/US2012/037073
§ 371 (c)(1),
(2), (4) Date: Apr. 16, 2014

(87) PCT Pub. No.: WO2012/154818
PCT Pub. Date: Nov. 15, 2012

(65) Prior Publication Data
US 2014/0370046 A1 Dec. 18, 2014

Related U.S. Application Data

(60) Provisional application No. 61/483,983, filed on May 9, 2011.

(51) Int. Cl.
| A61K 39/00 | (2006.01) |
| A61K 49/00 | (2006.01) |
| A61K 39/02 | (2006.01) |
| A61K 47/48 | (2006.01) |
| A61K 39/39 | (2006.01) |
| A61K 31/716 | (2006.01) |

(52) U.S. Cl.
CPC ...... *A61K 47/48284* (2013.01); *A61K 31/716* (2013.01); *A61K 39/39* (2013.01)

(58) Field of Classification Search
CPC ..... A61K 39/00; A61K 39/0002; A61K 39/02
USPC .............................. 424/9.1, 9.2, 184.1, 234.1
See application file for complete search history.

(56) References Cited

U.S. PATENT DOCUMENTS

| 6,294,321 B1 | 9/2001 | Wakshull et al. |
| 6,733,748 B2 | 5/2004 | Spaner |
| 7,981,447 B2 | 7/2011 | Cox |
| 2004/0127458 A1* | 7/2004 | Hunter ............................ 514/54 |
| 2008/0103112 A1 | 5/2008 | Magee et al. |
| 2011/0045049 A1 | 2/2011 | Rubin-Bejerano et al. |

FOREIGN PATENT DOCUMENTS

| WO | WO 96/14873 A2 | 5/1996 |
| WO | WO 2012/154818 A1 | 11/2012 |

OTHER PUBLICATIONS

PCT Patent Application No. PCT/US2012/037073, filed May 9, 2012; International Preliminary Report on Patentability dated Nov. 21, 2013; 7 pages.
PCT Patent Application No. PCT/US2012/037073, filed May 9, 2012; International Search Report/Written Opinion dated Jul. 3, 2012; 10 pages.
Allendorf, et al., "C5a-Mediated Leukotriene $B_4$-Amplified Neutrophil Chemotaxis Is Essential in Tumor Immunotherapy Facilitated by Anti-Tumor Monoclonal Antibody and β-Glucan", Jun 1, 2005, *J Immunol.*; 174(11):7050-6.
Hermanson, Chapter 2, "The Chemistry of Reactive Functional Groups", 1996, *Bioconjugate Techniques*, Academic Press, Waltham, Massachusetts; Cover page, publisher's page, and pp. 137-166.
Lavigne, et al., "β-Glucan Is a Fungal Determinant for Adhesion-Dependent Human Neutrophil Functions", Aug. 1, 2006, *J Immunol.*; 177(12):8667-8675.
Li, et al., "Yeast β-Glucan Amplifies Phagocyte Killing of iC3b-Opsonized Tumor Cells via Complement Receptor 3-Syk-Phosphatidylinositol 3-Kinase Pathway", Aug. 1, 2006, *J Immunol.*; 177(3):1661-9.
Salvador, et al., "Yeast-Derived β-Glucan Augments the Therapeutic Efficacy Mediated by Anti-Vascular Endothelial Growth Factor Monoclonal Antibody in Human Carcinoma Xenograft Models", Feb. 15, 2008, *Clinical Cancer Research*; 14:1239-1247.
Steinhagen et al., "TLR-based Immune Adjuvants", Apr. 12, 2011, *Vaccine*; 29(17):3341-3355. Epub Aug. 14, 2010.
Vasilakos, "Anti-tumor activity of soluble beta-1,3/1,6 glucans: structure matters," Poster and Abstract 5627 presented on Apr. 21, 2010, at the *AACR 101st Annual Meeting* 2010 sponsored by the American Association for Cancer Research, and held in Washington, D.C.: Apr. 17-21, 2010. Abstract 5627 also published in *Proceedings of the 101st Annual Meeting of the American Association for Cancer Research* Apr. 15, 2010 *Cancer Res.* ;70(8 Suppl):Abstract 5627.

* cited by examiner

*Primary Examiner* — Rodney P Swartz
(74) *Attorney, Agent, or Firm* — Mueting, Raasch & Gebhardt, P.A.

(57) ABSTRACT

Described herein are beta-glucan compounds, compositions, and methods. Generally, the methods exploit the observation that beta-glucan compounds can bind to B cells. Thus, the methods generally include administering a beta-glucan compound to a subject in an amount effective for the beta-glucan compound to bind to a B cell and modulate at least one biological function of the B cell.

22 Claims, 7 Drawing Sheets

BETA-GLUCAN COMPOUNDS, COMPOSITIONS, AND METHODS

CROSS-REFERENCE TO RELATED APPLICATION

This application is a U.S. National Stage Application of International Application No. PCT/US2012/037073, entitled β-GLUCAN COMPOUNDS, COMPOSITIONS, AND METHODS, filed on May 9, 2012, which claims priority to U.S. Provisional Patent Application Ser. No. 61/483,983, filed May 9, 2011, each of which is incorporated by reference herein in its entirety.

BACKGROUND

IMPRIME PGG (β(1,6)-[poly-1,3)-D-glucopyranosyl]-poly-b(1,3)-D-glucopyranose, Biothera, Eagan, Minn.) is a soluble form of yeast-derived β-glucan. Laminarin is another example of a β-1,3/1,6 glucan, however laminarin is derived from algae and differs chemically from IMPRIME PGG.

Yeast β-glucans are conserved microbial structures not found in mammalian cells. IMPRIME PGG is a soluble β-glucan isolated from yeast. Since IMPRIME PGG is a conserved microbial structure not found in mammals, and IMPRIME PGG is recognized by innate immune cells, IMPRIME PGG is classified as a pathogen-associated molecular pattern (PAMP). In general, PAMPs are microbial components that are first recognized by the innate immune system resulting in immune activation.

Activation of the innate immune system with soluble β-glucans can result in anti-tumor activity in mice (Allendorf et al., 2005, J Immunol., 174(11):7050-7056; Li et al., 2006, J Immunol., 177(3):1661-1669; Salvador et al., 2008, Clinical Cancer Research, 14:1239-1247). Unlike other PAMPs (e.g., LPS, Pam3Cys, poly I:C), IMPRIME PGG does not appear to induce overt production of pro-inflammatory cytokines such as, for example, the NF-κB-regulated cytokines tumor necrosis factor-α (TNF-α) and interferons (e.g., IFN-α and IFN-γ). Thus, IMPRIME PGG may modulate immune responses in a different manner than other PAMPs.

SUMMARY

In one aspect, this disclosure describes a method that generally includes administering to a subject an amount of a β-glucan compound effective to bind to B cells and modulate at least one biological function of the B cells.

In some embodiments, the β-glucan compound generally includes a β-glucan moiety and an active moiety. In some such embodiments, the active moiety can include an immunomodulator, an antibody, an antigen, a cytotoxic agent, a cytokine, an inhibitor of Bcl-2, a kinase inhibitor, an mTOR inhibitor, a proteosome inhibitor, or an immunosuppressive agent. In some such embodiments, the β-glucan moiety and the active moiety may be coupled through a covalent linkage. In other such embodiments, the β-glucan moiety and the active moiety may be coupled through an affinity linkage.

In some embodiments, the β-glucan can be a soluble β-glucan, while in other embodiments the β-glucan can be a particulate β-glucan.

In some embodiments, the β-glucan compound can include a derivatized β-glucan or a modified β-glucan.

In some embodiments, the biological function of the B cells comprises making an immunoglobulin.

In some embodiments, modulating at least one B cell biological function comprises killing B cells.

In another aspect, the invention provides a β-glucan compound that generally includes a β-glucan moiety coupled to an active moiety.

In some embodiments, the active moiety can include an immunomodulator, an antibody, an antigen, a cytotoxic agent, a cytokine, or an immunosuppressive agent. In some of these embodiments, the β-glucan moiety and the active moiety may be coupled through a covalent linkage. In other such embodiments, the β-glucan moiety and the active moiety may be coupled through an affinity linkage.

In some embodiments, the β-glucan moiety is derived from yeast. In some of these embodiments, the yeast can include *Saccharomyces cerevisiae*. In one particular embodiment, the β-glucan moiety can include β(1,6)-[poly-1,3)-D-glucopyranosyl]-poly-b(1,3)-D-glucopyranose.

In another aspect, this disclosure describes a pharmaceutical composition that generally includes a β-glucan compound as described herein.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2. A) IMPRIME PGG binding to B cells in whole blood. B) IMPRIME PGG binding to B cells in PBMCs. C) Laminarin binding to B cells in PBMCs.

FIG. 3. A) Surface CR2 expression on PBMC subsets. B) Blocking of IMPRIME PGG binding on B cells in whole blood by anti-CR2 antibody. C) Blocking of IMPRIME PGG binding on B cells in PBMCs by anti-CR2 antibody. (shaded peak—No IMPRIME PGG; open peaks—IMPRIME PGG+ Isotype ctrl and IMPRIME PGG+anti-CR2 blocking antibody).

FIG. 4. A) CR2 surface expression on human Daudi and Raji B cell tumor cell lines (shaded peak—isotype; open peak—anti-CR2). B) Binding of IMPRIME PGG to Daudi and Raji B cell tumor cell lines (shaded peak—No IMPRIME PGG; open peaks—50 mcg/mL IMPRIME PGG and 200 mcg/mL IMPRIME PGG).

DETAILED DESCRIPTION OF ILLUSTRATIVE EMBODIMENTS

The invention generally involves binding of β-glucan compounds to B cells, including B cell tumors, and methods that exploit this binding activity. As a result, β-glucan compounds may be used as a modulator of B cell function. Thus, β-glucan compounds may be used to target B cells in circumstances in which it may be desired to activate one or more B cell functions such as, for example, the production of a neutralizing or growth-inhibiting antibody. This may be useful for prophylactic or therapeutic treatments of, for example, infectious and/or neoplastic conditions. Alternatively, β-glucan compounds may be used to target B cells in circumstances in which it may be desirable to inhibit B cell functions. This may be useful for treatments of, for example, B cell neoplasms such as, for example, B cell chronic lymphocytic leukemia, or autoimmune conditions such as, for example, any condition in which one component of the condition involves dysregulation of antibody production such as, for example, Lupus or rheumatoid arthritis.

Thus, in one aspect, the invention provides methods that generally include administering to a subject an amount of a β-glucan compound effective to bind to B cells and modulate at least one biological function of the B cells.

The β-glucan compound—or as in certain embodiments discussed in more detail below, a β-glucan moiety of a β-glucan compound—can be or be derived from, for example, β-glucan derived from a fungal yeast source such as, for example, *Saccharomyces cerevisiae, Torula* (*candida utilis*), *Candida albicans, Pichia stipitis*, or any other yeast source; β-glucan derived from another fungal source such as, for example, scleroglucan from *Sclerotium rofsii* or any other non-yeast fungal source; β-glucan from an algal source such as, for example, laminarin or phycarine from *Laminaria digitata* or any other algal source; β-glucan from a bacterial source such as, for example, curdlan from *Alcaligenes faecalis* or any other bacterial source; β-glucan from a mushroom source such as, for example, schizophyllan from *Schizophyllan commune, lentinan* from *Lentinan edodes*, grifolan from *Grifola frondosa*, ganoderan from *Ganoderma lucidum*, krestin from *Coriolus versicolor*, pachyman from *Poria cocos* Wolf, or any other mushroom source; β-glucan derived from a cereal grain source such as, for example, oat glucan, barley glucan, or any other cereal grain source; β-glucan derived from a lichen source such as, for example, pustulan from *Umbilicaris pustulata*, lichenan from *Cetraria islandica*, or any other lichen source. The form of glucan used to make these conjugates can be either soluble or insoluble in water. In some embodiments, the β-glucan or β-glucan moiety is water-soluble.

In some embodiments, the β-glucan or β-glucan moiety may be, or be derived from *Saccharomyces cerevisiae*. One such form of β-glucan derived from *Saccharomyces cerevisiae* is β(1,6)-[poly-1,3)-D-glucopyranosyl]-poly-b(1,3)-D-glucopyranose. β(1,6)-[poly-1,3)-D-glucopyranosyl]-poly-b(1,3)-D-glucopyranose can be provided in various forms. One form of this β-glucan is a particulate form described, for example, in U.S. Pat. No. 7,981,447. The β-glucan can form particles ranging in size from a minimum of 0.1 μM to about 6.0 μM. In some cases, the particles are not water-soluble. A water-soluble form of this β(1,6)-[poly-1,3)-D-glucopyranosyl]-poly-b(1,3)-D-glucopyranose is referred to herein as IMPRIME PGG and is described in, for example, U.S. Patent Application Publication No. US2008/0103112 A1. Laminarin is another example of a β-1,3/1,6 glucan. Laminarin, however, is derived from algae and differs chemically from the particulate and IMPRIME PGG forms of yeast β-glucan. Some of those differences are reflected in Table 1.

TABLE 1

| Compound | IMPRIME PGG | Laminarin |
|---|---|---|
| Biological source | *Saccharomyces cerevisiae* (yeast) | *Laminaria digitata* (algae) |
| Average Mol. Wt. | 150,000 | 8,000 |
| % Branching | 4% | 8% |

In some embodiments, the β-glucan compound can include a β-glucan moiety coupled to an active moiety. As used herein, the term "moiety" and variations thereof refer to a portion of a chemical compound that exhibits a particular character such as, for example, a particular biological or chemical function such as, for example, immunomodulation, cytotoxicity, solubility, bioavailability, metabolism and/or target specificity.

The active moiety may include any compound that possesses a particular activity toward B cells. The activity may, for example, include modulating one or more B cell biological functions or cytotoxic activity. As used herein, "modulate" and variations thereof refer to a substantial increase or decrease in biological function. A substantial increase or decrease in biological activity is an increase or decrease beyond a predetermined threshold increase or decrease in the biological function. Thus, the active moiety may induce or, alternatively, inhibit one or more B cell biological functions. As used herein, "induce" and variations thereof refer to any measurable increase in biological function. For example, induction of B cells may be reflected by, for example, inducing the B cells to produce an antigen-specific antibody. "Inhibit" and variations thereof refer to any measurable reduction of biological function. For example, inhibition of B cells can include, for example, causing the B cells to produce less antigen-specific antibody than in the absence of the inhibitory stimulus. The extent of inhibition may be characterized as a percentage of a normal level of activity. "Biological function" refers to cellular activity (e.g., antibody production, cytokine production, surface receptor modulation, cellular proliferation) that is characteristic of an identified cell type.

The active moiety may be, or be derived from, an adjuvant or immunomodulator. Exemplary immunomodulators include, for example, pathogen-associated molecular patterns (PAMPs) and/or danger-associated molecular patterns (DAMPs).

PAMPs include molecules that are often associated with groups of pathogens and are recognized by cells of the innate immune system. PAMPs can be referred to as small molecular motifs conserved within a class of microbes. They are recognized by Toll-like receptors (TLRs) and other pattern recognition receptors (PRRs). PAMPs can activate innate immune responses by identifying some conserved non-self molecules. Bacterial lipopolysaccharide (LPS), an endotoxin found on the bacterial cell membrane of many bacteria, is an exemplary PAMP. LPS is specifically recognized by TLR 4, a recognition receptor of the innate immune system. Other PAMPs include, for example, bacterial flagellin (recognized by TLR 5), lipoteichoic acid from Gram positive bacteria, peptidoglycan, and nucleic acid variants normally associated with viruses, such as, for example, double-stranded RNA (dsRNA, recognized by TLR 3), unmethylated CpG motifs (recognized by TLR 9), or certain imidazoquinoline amine derivatives that are recognized by TLR 7 and/or TLR 8.

DAMPs include molecules that can initiate and perpetuate immune response in the noninfectious inflammatory response. Many DAMPs are nuclear or cytosolic proteins with defined intracellular functions that, when released outside the cell following tissue injury, move from a reducing to an oxidizing milieu resulting in their functional denaturation. Also, following necrosis, tumor DNA may be released into the extranuclear space/extracellular microenvironment and functions as a DAMP. DAMPs can vary greatly depending on the type of cell (e.g., epithelial versus mesenchymal) and injured tissue. Protein DAMPs include, for example, intracellular proteins such as, for example, heat-shock proteins or HMGB1 (high-mobility group box 1), and proteins derived from the extracellular matrix that are generated following tissue injury, such as hyaluronan fragments. Examples of non-protein DAMPs include ATP, uric acid, heparin sulfate, and DNA.

Thus, in some embodiments, the active moiety may be, or be derived from a PAMP or a DAMP such as, for example, an agonist of one or more Toll-like receptors (TLRs). In some embodiments, the active moiety may be an agonist of TLR 1 (e.g., a triacyl lipopeptide), an agonist of TLR 2 (e.g. lipoteichoic acid), an agonist of TLR 3 (e.g., dsRNA), an agonist of TLR 4 (e.g., lipopolysaccharide), an agonist of TLR 5 (e.g., flagellin), an agonist of TLR 6 (e.g., peptidoglycan), an agonist of TLR 7 (e.g., ssRNA, imidazoquinolines, loxoribine), an agonist of TLR 8 (e.g., imidazoquinolines, loxoribine), or an agonist of TLR 9 (e.g., an unmethylated CpG oligonucleotide).

In other embodiments, the active moiety can include, or be derived from an antibody. Certain antibodies are known to activate B cells and, therefore, induce B cells biological functions. Such an antibody can include or be derived from, for example, an anti-CD20 antibody (e.g., rituximab), an anti-CD22 antibody (e.g., epratuzumab), an anti-CD70 antibody, an anti-CD40 antibody, or an anti-CD137 antibody. CD137 is also known as 4-1BB, so an anti-CD137 antibody may alternatively be referred to as an anti-4-1BB antibody. An active moiety may include an immunologically active fragment of an antibody such as, for example, a scFv, a Fab, a F(ab')$_2$, a Fv, or other modified antibody fragment.

In other embodiments, the active moiety can include an antigen. As used herein, "antigen" and variations thereof refer to any material capable of raising an immune response in a subject challenged with the material. In various embodiments, an antigen may raise a cell-mediated immune response, a humoral immune response, or both. Suitable antigens may be synthetic or occur naturally and, when they occur naturally, may be endogenous (e.g., a self-antigen) or exogenous. Suitable antigenic materials include but are not limited to peptides or polypeptides; lipids; glycolipids; polysaccharides; carbohydrates; polynucleotides; prions; live or inactivated bacteria, viruses, fungi, or parasites; and bacterial, viral, fungal, protozoal, tumor-derived, or organism-derived immunogens, toxins or toxoids.

Thus, exemplary antigens include viral antigens such as, for example, antigens associated with influenza, Hepatitis A, Hepatitis B, Hepatitis C, adenovirus, Herpes Simplex B, or other suitable virus.

Exemplary antigens also can include an antigen associated with a particular type of neoplasm or tumor. Such antigens include, for example, MUC-1, CA 125, telomerase/hTERT, PSA, NY-ESO-1, MAGE, AML1 fusions, EGFR, HER2/NEU, gp100, WT1, CEA, or other antigen having a known association with one or more tumors.

Exemplary antigens also can include bacterial antigens such as, for example, tetanus toxoid, diphtheria toxoid, a *Staphylococcus* spp. antigen, a *Pneumococcus* spp. antigen, a *Klebsiella* spp. antigen, or another bacterial antigen.

Exemplary antigens also can include parasitic antigens such as, for example, a *Trypanosoma* spp. antigen, a *Toxoplasma* spp. antigen, a *Leishmania* spp. antigen, a *Plasmodium* spp. antigen, a *Schistosoma* spp. antigen, or another parasitic antigen.

In other embodiments, the active moiety can include, or be derived from, a cytotoxic agent. Such embodiments may have particular utility where the B cell may be targeted for killing such as, for example, in the case of certain B cell lymphomas. Thus, the targeted delivery of such agents can permit systemic delivery while reducing the likelihood, extent, and/or severity of systemic side effects. Cytotoxic agents can include, for example, chemotherapeutic agents such as, for example, cisplatin, fludarabine, cyclophosphamide, doxorubicin, vincristine, carboplatin, ifosfamide, etoposide, cytarabine, paclitaxel, or ABRAXANE (Celgene Corp., Summit, N.J.). Other exemplary cytotoxic agents include, for example, ricin A chain or diphtheria toxin. Cytotoxic agents also can include certain radioactive isotopes such as, for example, yttrium-90 or iodine-131.

In some embodiments, the active moiety can include a cytokine such as, for example, IL-10, IL-12, or recombinant forms thereof.

In other embodiments, the active moiety can be, or be derived from, immunosuppressive agents. Exemplary immunosuppressive agents include, for example, a corticosteroid, tacrolimus, or methotrexate.

In other embodiments, the active moiety can be, or be derived from, inhibitors of the Bcl-2 family of proteins. Exemplary inhibitors include, for example, small molecules, antisense oligonucleotides, or Bcl-2 homology 3 (BH3) mimetic peptides.

In other embodiments, the active moiety can be, or be derived from, small molecule inhibitors of kinases that modulate B cell function. Exemplary examples of kinases include, for example, Bruton's tyrosine kinase (Btk), spleen tyrosine kinase (Syk), or phosphoinositide-3 kinase (PI3K).

In other embodiments, the active moiety can be, or be derived from, small molecule inhibitors of other targeted kinases for oncology. Exemplary examples of targeted kinases include, for example, Bcr-Abl, PDGFR, c-KIT, DDR1, EGFR, ERBB2 (HER2), HER4, VEGFR, VEGFR (b-raf), SRC family, or TEC family. Exemplary examples of approved kinase inhibitors that could be the active moiety, or from which the active moiety may be derived, include, for example, imatinib (e.g., GLEEVEC, Novartis Pharmaceuticals Corp., East Hanover, N.J.), nilotinib (e.g., TASIGNA, Novartis Pharmaceuticals Corp., East Hanover, N.J.), erlotinib (e.g., TARCEVA, Genentech, Inc., South San Francisco, Calif.), gefitinib (e.g., IRESSA, AstraZeneca Pharmaceuticals LP, Wilmington, Del.), sorafenib (e.g., NEXAVAR, Onyx Pharmaceuticals, Inc., South San Francisco, Calif.), sunitinib (e.g., SUTENT, Pfizer, Inc., New York, N.Y.), lapatinib (e.g., TYKERB, GlaxoSmithKline plc, Philadelphia, Pa.), and dasatinib (e.g., SPRYCEL, Bristol-Myers Squibb, Princeton, N.J.).

In other embodiments, the active moiety can be, or be derived from, mTOR (mammalian target of rapamycin) inhibitors (e.g., approved mTOR inhibitors include everolimus (e.g., AFINITOR and ZORTRESS, Novartis Pharmaceuticals Corp., East Hanover, N.J.) and temsirolimus (TORISEL, Pfizer, Inc., New York, N.Y.).

In other embodiments, the active moiety can be, or be derived from, proteasome inhibitors that inhibit the NF-κB pathway such as, for example, bortezomib (e.g., VELCADE, Millennium Pharmaceuticals, Inc., Cambridge, Mass.)

In some embodiments, the β-glucan moiety may be coupled to the active moiety. The β-glucan moiety and the active moiety may be covalently coupled or, in some embodiments, may include at least one affinity or ionic bond. As used herein, "covalently coupled" refers to direct or indirect coupling of two components exclusively through covalent bonds. Direct covalent coupling may involve direct covalent binding between an atom of the β-glucan moiety and an atom of the active moiety. Alternatively, the covalent coupling may occur through a linking group covalently attached to the β-glucan moiety, the active moiety, or both, that facilitates covalent coupling of the β-glucan moiety and the active moiety. Indirect covalent coupling may include a third component such as, for example, a solid support to which the β-glucan moiety and the active moiety are separately covalently attached. As used herein, "covalently coupled" and "covalently attached" are used interchangeably.

When present, the linking group can be any suitable organic linking group that allows the β-glucan moiety to be covalently coupled to the active moiety while preserving the B cell targeting activity of the β-glucan moiety and an effective amount of activity of the active moiety.

The linking group can includes a reactive group capable of reacting with the active moiety to form a covalent bond. Suitable reactive groups include, for example, those discussed in Hermanson, G. (1996), *Bioconjugate Techniques*, Academic Press, Chapter 2 "The Chemistry of Reactive Functional Groups", 137-166. For example, the linking group may react with a primary amine (e.g., an N-hydroxysuccinimidyl ester or an N-hydroxysulfosuccinimidyl ester); it may react with a sulfhydryl group (e.g., a maleimide or an iodoacetyl), or it may be a photoreactive group (e.g. a phenyl azide including 4-azidophenyl, 2-hydroxy-4-azidophenyl, 2-nitro-4-azidophenyl, and 2-nitro-3-azidophenyl).

A chemically active group accessible for covalent coupling to the linking group includes groups that may be used directly for covalent coupling to the linking group or groups that may be modified to be available for covalent coupling to the linking group. For example, suitable chemically active groups include but are not limited to primary amines and sulfhydryl groups. Because certain active moieties—e.g., proteins and other peptides—may include a plurality of chemically active groups, certain β-glucan compounds may include a plurality of β-glucan moieties coupled to an active moiety.

Certain β-glucan compounds may contain chemical associations between the β-glucan moiety and the active moiety other than covalent coupling. For example, a β-glucan compound may include an affinity interaction between the β-glucan moiety and the active moiety. Avidin-biotin affinity represents one example of a non-covalent interaction that may be utilized to couple an active moiety and a β-glucan moiety. For example, a biotin molecule may be covalently attached to a proteinaceous active moiety via one of a number of functional groups present on amino acids (e.g., primary amines or sulfhydryl groups), a β-glucan may be coupled to an avidin molecule by appropriate derivatization of the β-glucan moiety, and the two moieties may be non-covalently coupled to one another through the avidin-biotin affinity interaction. Methods for biotinylating proteins and linking chemical groups to avidin are well known to one of skill in the art. Alternative affinity interactions that may be useful for making β-glucan compounds include, for example, antigen/antibody interactions and glycoprotein/lectin interactions.

In some embodiments, the β-glucan compound can include a derivatized β-glucan. Generally, β-glucan may be derivatized by, for example, alkylation, adding an amine-containing moiety, side chain modification, or oxidation of primary hydroxyl groups to yield glucuronic acid moieties.

Thus, the methods described herein can exploit the B cell binding properties of the β-glucan compound to directly modulate one or more B cell biological functions or, alternatively, to deliver an active agent that can modulate one or more B cell biological functions. Since the β-glucan compound can modulate B cell biological functions, the β-glucan compounds described herein also can be used to modulate B cell-induced functions or phenomena.

Figure 7:
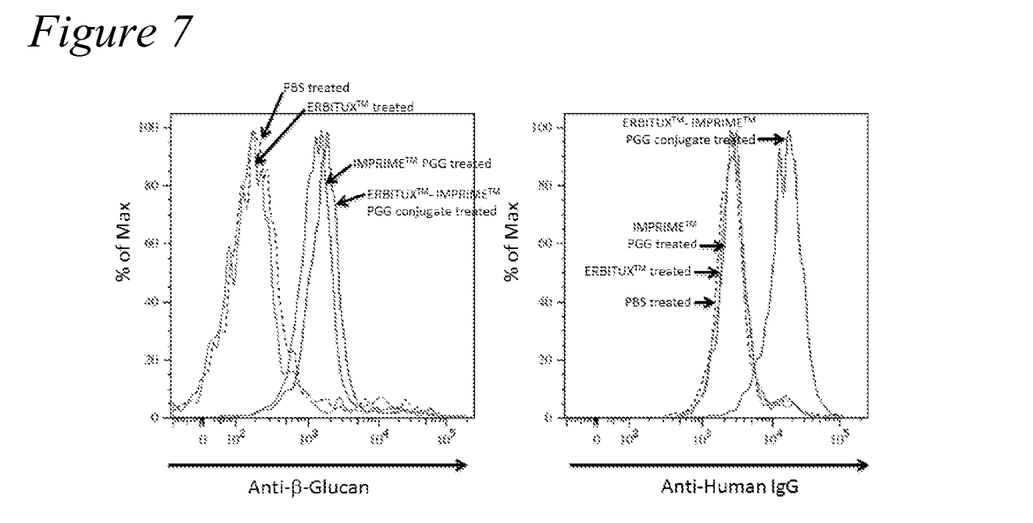
FIG. 7. Targeted binding of β glucan (IMPRIME PGG) and β-glucan conjugate to B cells. (A) β-glucan (IMPRIME PGG-treated) and β glucan-ERBITUX conjugate (ERBITUX-IMPRIME PGG conjugated-treated) bind to B cells and are detected using an anti-β-glucan antibody. (B) β-glucan-ERBITUX conjugate binds to B cells and is detected using an anti-Human IgG antibody.
Figure 8:
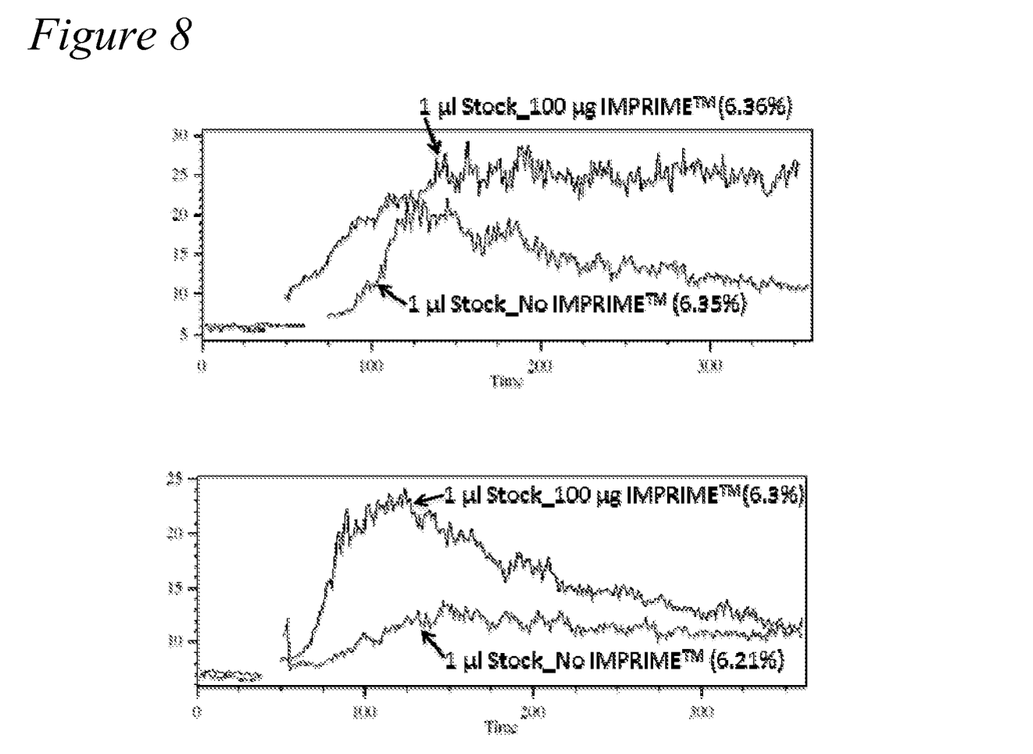
FIG. 8. Calcium flux in cells treated in vitro with soluble β-glucan, then stimulated with IgM.

The β-glucan compound can, therefore, be used to target and activate B cells. Such a method may be used, for example, to induce neutralizing or growth-inhibiting antibody for treating an infectious disease or cancer. As another example, FIG. 7 shows the targeted delivery of a therapeutic compound—ERBITUX (Eli Lilly and Co., New York, N.Y. and Bristol-Myers Squibb Co., Princeton, N.J.)—to B cells by conjugating the compound to a β-glucan (IMPRIME PGG).

β-glucan compounds described herein can be used to target immune potentiating or immune modulating agents to B cells. For example, one may target an antigen to B cells in order to generate an immune response to that antigen. The data presented in FIG. 8 demonstrate that IMPRIME PGG can activate B cells. Calcium flux is an indicator of B cell activation. FIG. 8 shows that B cells incubated in the presence of IMPRIME PGG and then stimulated with goat anti-human IgM exhibit an increased and prolonged period of calcium flux and, therefore, an increased and prolonged period of activation. This native B cell activating activity of certain β-glucans may be used to induce a B cell response against a particular antigen by coupling an antigen of interest to the B cell-activating β-glucan.

Figure 9:
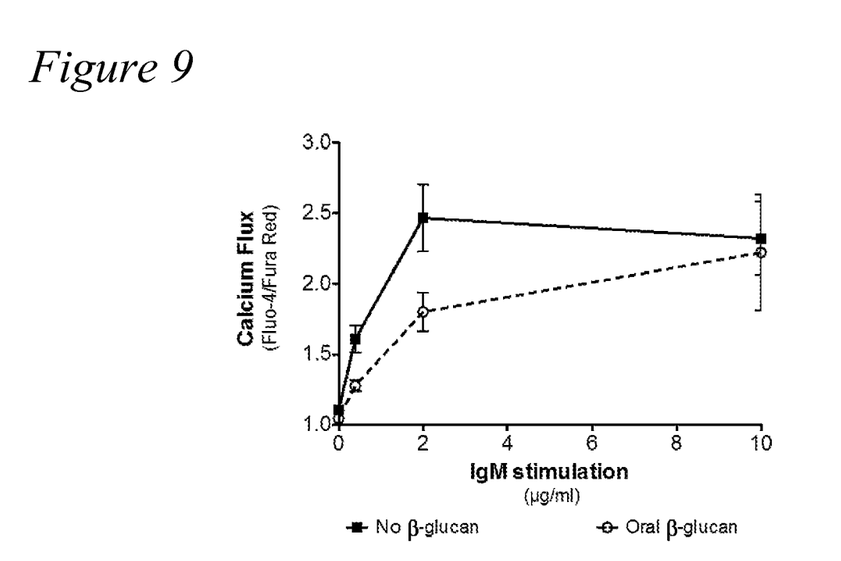
FIG. 9. Calcium flux in cells of subjects treated in vivo with particulate β-glucan, then stimulated with IgM.

In other cases, the β-glucan may be used to target and inhibit B cell function. Such a method may be used, for example, to inhibit antibody production by B cells where B cell function is dysregulated such as, for example, in autoimmune conditions such as Lupus or rheumatoid arthritis. For example, data presented in FIG. 9 demonstrate that a particulate form of β-glucan, orally administered to a subject, can decrease calcium flux in B cells stimulated with goat anti-human IgM. Thus, activation of B cells in the β-glucan-treated subjects was inhibited compared to the untreated control subjects. This B cell inhibiting activity of certain β-glucans may be used to inhibit the B cell response against a particular antigen by coupling the antigen of interest to the B cell-inhibiting β-glucan.

As yet another example, one may target an inducer of immunoglobulin production to B cells—e.g., a TLR7 agonist or a TLR9 agonist—in order to generate antibody against infectious diseases and cancer. Non-targeted TLR agonists can be poorly tolerated and may have relatively narrow therapeutic window. Thus, targeting their delivery to B cells as part of a β-glucan molecule can allow systemic delivery of the TLR agonists with targeted activity, thereby reducing potential systemic side effects of such agents. Furthermore, β-glucans can act as vaccine adjuvants. Thus, a β-glucan compound that includes a β-glucan moiety and, for example, a PAMP or a DAMP, used in combination with an antigen may enhance immune responses and reduce systemic exposure of the DAMP and/or PAMP. Thus, a β-glucan compound that includes an immunomodulator as an active moiety, when formulated with an antigen in a vaccine, may be retained at a site of injection and, therefore, may enhance the adjuvant activity of the active moiety. Such a β-glucan compound may not only be targeted to B cells, but also may activate B cells near the introduced vaccine antigen, thereby enhancing the presentation of the desired antigen to the immune system. Moreover, a β-glucan compound that includes a small molecule TLR agonist—e.g., an imidazoquinoline amine—as an active moiety can be retained at the site of administration (e.g., injection or vaccination). Some small molecule immunomodulators can be dispersed systemically due to their small size and, consequently, be of limited efficacy at the site of administration. When coupled to a β-glucan as the active moiety of a β-glucan compound, however, the β-glucan/immunomodulator β-glucan compound may be of sufficient size so that the small molecule active moiety is better retained at the site of administration.

Certain β-glucan molecules described herein can be used to eliminate B cells that are neoplastic or that produce autoantibodies. In these embodiments, a cytotoxic agent may be targeted to B cells by coupling the cytotoxic active agent to a β-glucan moiety.

In still other cases, β-glucan compounds described herein may be used to target B cell activators to B cells so that the combination of the B cell activator and the β-glucan moiety can produce additive or synergistic effects.

Thus, one or more β-glucan compounds described herein may be formulated in a composition along with a "carrier." As used herein, "carrier" includes any solvent, dispersion medium, vehicle, coating, diluent, antibacterial and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions.

As used herein, "pharmaceutically acceptable" refers to a material that is not biologically or otherwise undesirable, i.e., the material may be administered to an individual along with the β-glucan compound without causing any undesirable biological effects or interacting in a deleterious manner with any of the other components of the pharmaceutical composition.

One or more β-glucan compounds may be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Such pharmaceutical compositions may be used in methods for treating certain conditions where the condition may be treatable through modulation of B cell biological function. As noted above, such B cell modulation can include, depending upon the specific condition, increasing B cell biological function, decreasing B cell biological function, or targeted killing of B cells.

As used herein, "treat," "treating," or variations thereof refer to reducing, limiting progression, ameliorating, or resolving, to any extent, the symptoms or signs related to a condition. "Ameliorate" refers to any reduction in the extent, severity, frequency, and/or likelihood of a symptom or clinical sign characteristic of a particular condition. "Sign" or "clinical sign" refers to an objective physical finding relating to a particular condition capable of being found by one other than the patient. "Symptom" refers to any subjective evidence of disease or of a patient's condition.

The methods may be used to treat a condition prophylactically or therapeutically. As used herein, "prophylactic" and variations thereof refer to a treatment that limits, to any extent, the development and/or appearance of a symptom or clinical sign of a condition. In many cases, prophylactic treatment can occur before any symptom or clinical sign of the condition is apparent. As used herein, "therapeutic" and variations thereof refer to a treatment that ameliorates one or more existing symptoms or clinical signs associated with a condition. "Treatment" refers to a course of action—or one of a series of actions—for treating a condition.

A formulation may be conveniently presented in unit dosage form and may be prepared by methods well known in the art of pharmacy. Methods of preparing a composition with a pharmaceutically acceptable carrier include the step of bringing the one or more β-glucan compounds into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

One or more β-glucan compounds may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

Generally, the methods include administering to a subject in need of treatment an amount of a β-glucan compound described herein effective to modulate at least one B cell biological function.

The amount of β-glucan compound administered can vary depending on various factors including, but not limited to, the specific β-glucan compound or compounds being administered, the weight, physical condition, and/or age of the subject, and/or the route of administration. Thus, the absolute weight of β-glucan compound included in a given unit dosage form can vary widely, and depends upon factors such as the species, age, weight and physical condition of the subject, as well as the method of administration. Accordingly, it is not practical to set forth generally the amount that constitutes an amount of β-glucan compound effective for all possible applications. Those of ordinary skill in the art, however, can readily determine the appropriate amount with due consideration of such factors.

In some embodiments, the methods of the present invention include administering sufficient β-glucan compound to provide a dose of, for example, from about 100 ng/kg to about 50 mg/kg to the subject, although in some embodiments the methods may be performed by administering the β-glucan compound in a dose outside this range. In some of these embodiments, the method includes administering sufficient β-glucan compound to provide a dose of from about 10 µg/kg to about 5 mg/kg to the subject, for example, a dose of from about 100 µg/kg to about 1 mg/kg.

Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2$ (wt $kg^{0.425}$×height $cm^{0.725}$)×0.007184.

In some embodiments, the methods of the present invention may include administering sufficient β-glucan compound to provide a dose of, for example, from about 0.01 mg/$m^2$ to about 1000 mg/$m^2$ such as, for example, a dose of about 500 mg/$m^2$. In some cases, a β-glucan compound can be administered at one initial dose of, for example, 500 mg/$m^2$, then followed by subsequent lesser doses such as, for example, 250 mg/$m^2$.

In some embodiments, β-glucan compound may be administered, for example, from a single dose to multiple doses per week, although in some embodiments the methods of the present invention may be performed by administering β-glucan compound at a frequency outside this range. In certain embodiments, β-glucan compound may be administered from about once every 12 weeks, once every eight weeks, once every four weeks, or once every week.

As used herein, the term "and/or" means one or all of the listed elements or a combination of any two or more of the listed elements; the term "comprises" and variations thereof do not have a limiting meaning where these terms appear in the description and claims; unless specifically stated otherwise, "a," "an," "the," and "at least one" are used interchangeably and mean one or more than one; and recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiment can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Figure 1:
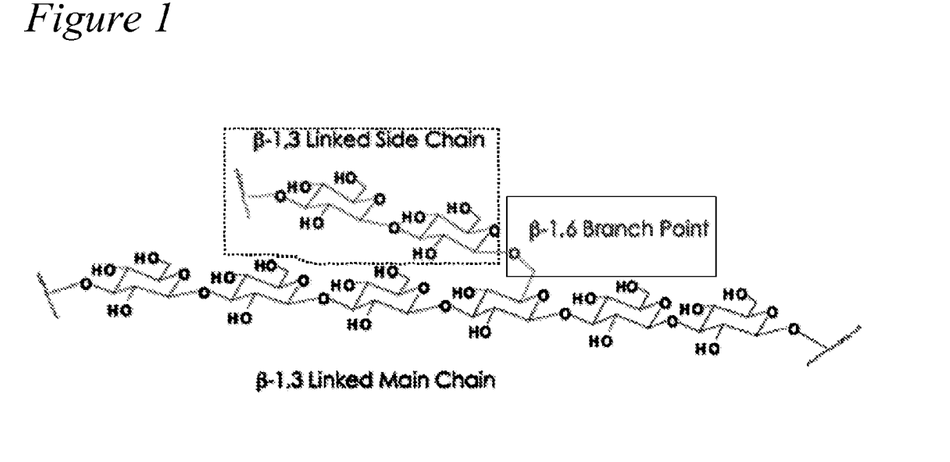
FIG. 1. Truncated structure of β(1,6)-[poly-1,3)-D-glucopyranosyl]-poly-b(1,3)-D-glucopyranose.
Figure 2A:
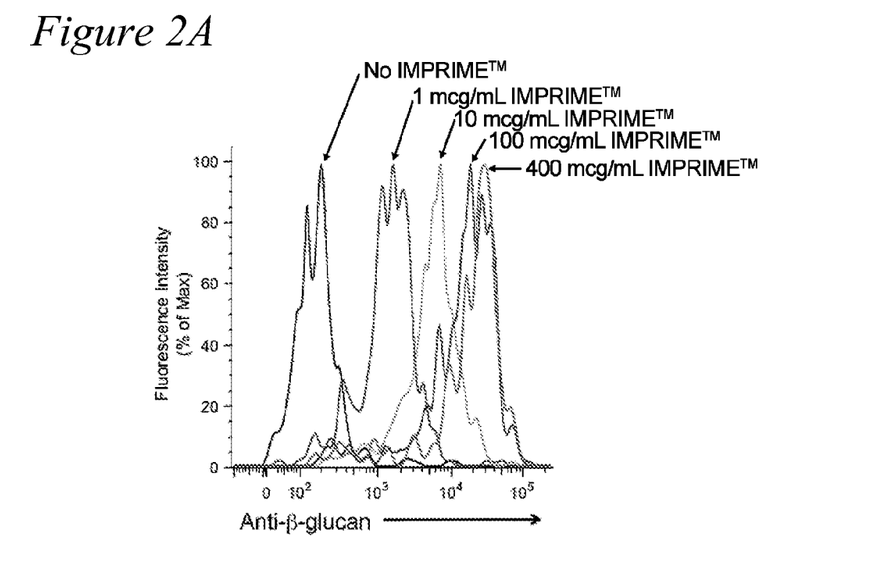
Figure 2B:
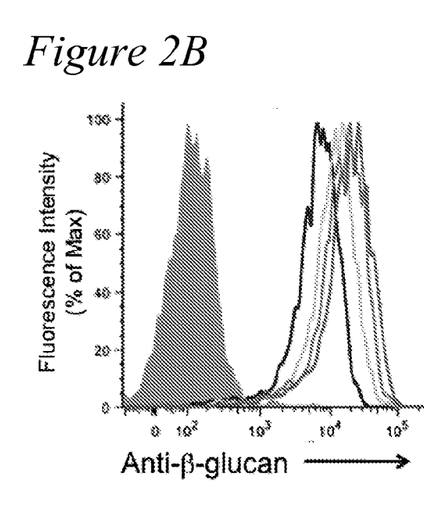
Figure 2C:
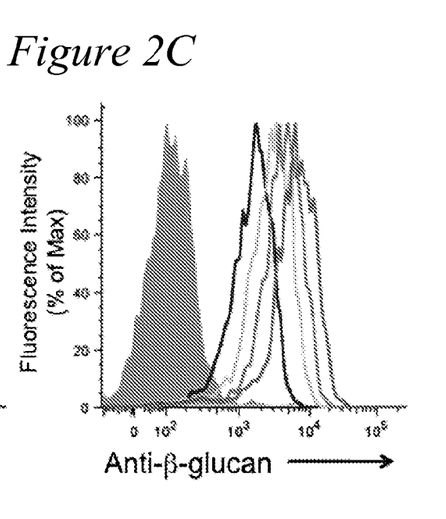

FIG. 2 demonstrates that some β-glucans, such as IMPRIME PGG and Laminarin, bind directly to human B cells in whole blood and enriched peripheral blood mononuclear cell (PBMC) population in a concentration-dependent manner. This ability was evaluated by comparing the levels of B cell-bound β-glucans detected by BfD IV, a monoclonal antibody (MAb) specific for β-1,3/1,6 glucans (U.S. Pat. No. 6,294,321). The histograms in FIG. 2 show the median fluorescence intensity (MFI) of BfD IV staining of various concentrations of β-glucans on B cells in whole blood (A) and enriched PBMC (B and C).

β-Glucan Binding Methodology:

A) Binding in Whole Blood:

Blood was collected from a healthy donor with 10 Units/mL Heparin. 100 µL of blood was mixed with IMPRIME PGG concentrations and incubated at 37° C. for 60 minutes. Cells were washed with 2 mL of PBS and supernatant removed by aspiration. Cells were then stained with 20 µL of BfD IV (U.S. Pat. No. 6,294,321) for 30 minutes before washing again with PBS. 10 µL of goat anti-mouse IgM FITC added to stain for BfD IV positive cells, while 10 µL of anti-CD19 APC was added to stain the B cell population for FACS analysis. Cells were incubated for 30 minutes at room temperature before washing with PBS. The red cells in the blood were lysed by the addition of 2 mL of BD Lyse and fixed with 2% paraformadehyde before analysis on an LSR II flow cytometer. Analysis was performed using FlowJo software. Results are shown in FIG. 2A.

B) Binding in PBMC:

Enriched PBMC were resuspended at 1×$10^6$ cells/mL in RPMI 1640 supplemented with 10% serum. The β-glucans (IMPRIME PGG (B) and laminarin (C)) at various hexose concentration were added to the cells and incubated in a 37° C., 5% CO2 humidified incubator for two hours. After incubation, cells were washed twice with FACS buffer (HBSS supplemented with 1% FBS and 0.1% sodium azide) to remove any unbound β-glucan, and subsequently treated with Fc block. After the Fc block step, cells were stained with the monoclonal antibody BfD IV (U.S. Pat. No. 6,294,321) for 30 minutes at 4° C. and washed twice with cold FACS buffer. Cells were then incubated with FITC-conjugated F(ab')$_2$ goat anti-mouse IgM for 30 minutes at 4° C. and washed once with cold FACS buffer before fixing with 1% paraformaldehyde. Events were collected on a LSRII flow cytometer and analysis was performed using FlowJo software. Results are shown in FIG. 2B (IMPRIME PGG) and FIG. 2C (laminarin).

Example 2

Figure 3A:
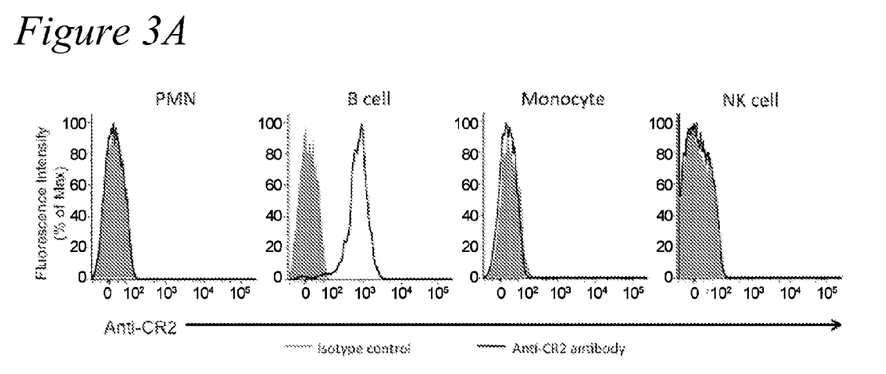

This example demonstrates that IMPRIME PGG binds to complement receptor 2, (CR2; aka CD21) on B cells. FIG. 3A shows that CR2 is abundantly expressed on human B-cells, but not on monocytes, neutrophils, or NK cells.

Figure 3B:
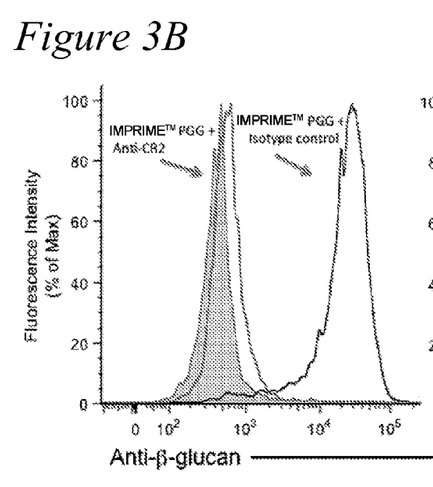
Figure 3C:
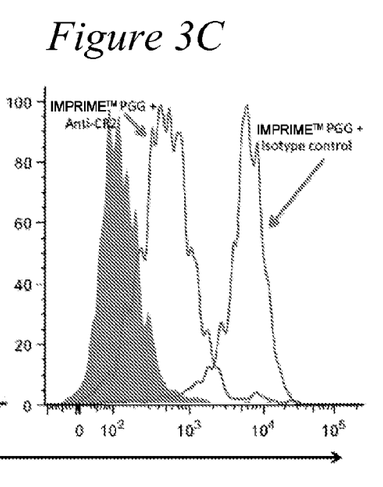

CR2 Staining Methodology:

Enriched PMNs, B cells, monocytes, or NK cells were resuspended at 1×$10^6$ cells/mL in FACS buffer (HBSS supplemented with 1% FBS and 0.1% sodium azide were stained with PE-conjugated anti-CR2 mouse Ab (LT-21) or mouse IgG1 isotype control and subsequently analyzed by flow cytometry. Results are shown in FIG. 3A.

β-Glucan Binding and CR2 Blocking Methodology:

Whole blood or PBMC were pre-incubated with specific receptor blocking antibodies or the relevant isotype controls at 4° C. for 30-45 minutes before addition of IMPRIME PGG at 100 µg/mL. Binding to B cells was performed as described in Example 1. Clone 1048, the mouse mAb against CR2, and mouse IgG1 isotype control was used at 10

μg/mL/1×10⁶ cells. Results are shown in FIG. 3B (Whole Blood) and FIG. 3C (PBMC).

Example 3

Figure 4A:
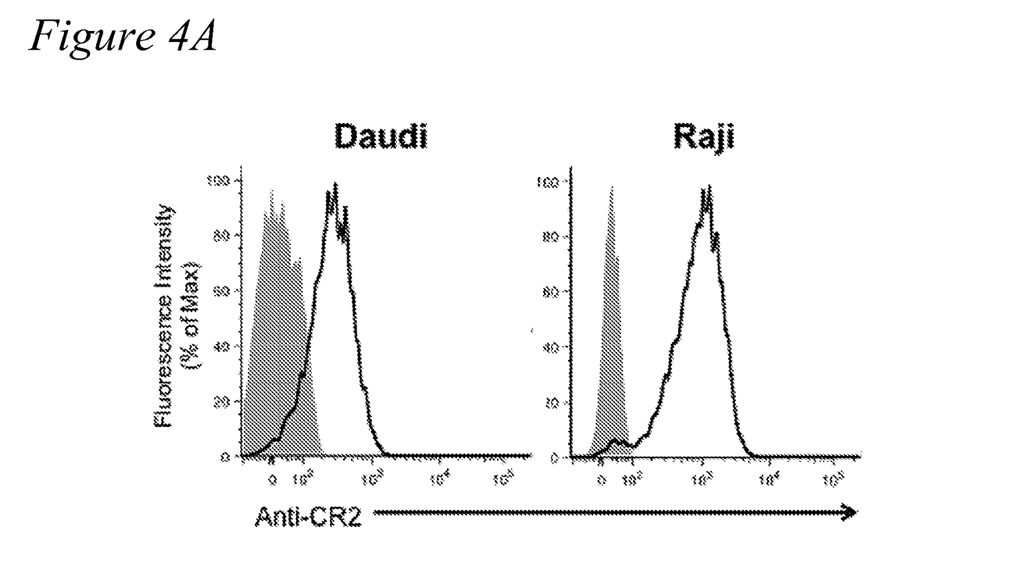
Figure 4B:
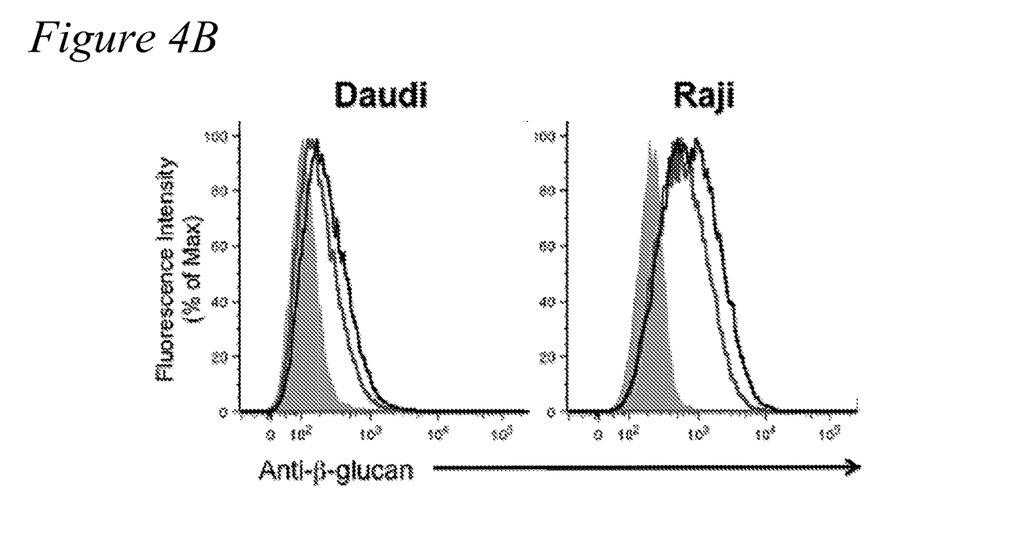

This example demonstrates that IMPRIME PGG not only binds to normal human cells, but also to B cell tumor lines. The histograms in FIG. 4 show that a) human B-cell tumor lines, Daudi and Raji express CR2, and b) IMPRIME PGG bound to these tumor lines in a concentration-dependent manner.

Staining of CR2 and Binding of IMPRIME PGG to B-Cell Lines Methodology:

Daudi or Raji cells, resuspended at 1×10⁶ cells/mL in FACS buffer (HBSS supplemented with 1% FBS and 0.1% sodium azide were stained with PE-conjugated anti-CR2 (LT-21) mouse mAb or mouse IgG1 isotype control and subsequently analyzed by flow cytometry as described in Example 1. Results are shown in FIG. 4A and FIG. 4B.

Example 4

Figure 5:
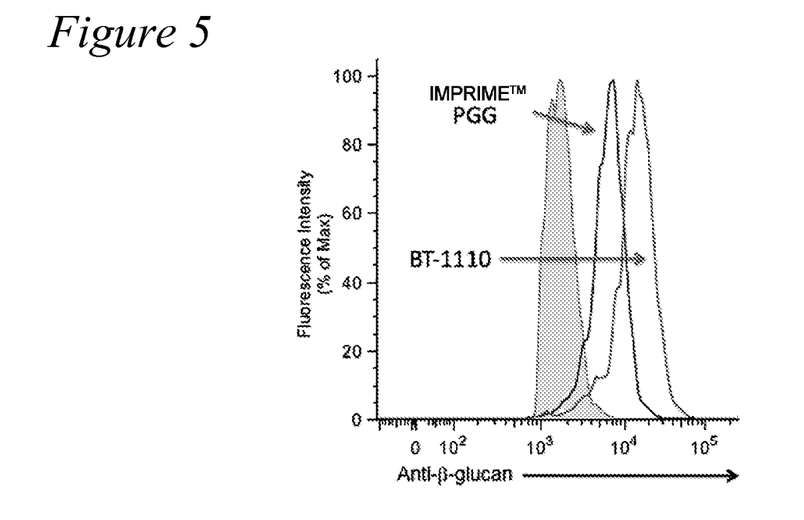
FIG. 5. IMPRIME PGG vs. BSA-conjugated IMPRIME PGG (BT-1110) binding to human B cells in whole blood.

This example demonstrates that conjugating bovine serum albumin (BSA) to IMPRIME PGG enhances its binding capacity to human B cells. The histogram in FIG. 5 shows that the mean fluorescent intensity (MFI) of BfD IV staining on IMPRIME PGG-BSA conjugate (BT-1110)-treated B cells is higher at the tested concentration (50 μg/mL) compared to parent cells treated with unconjugated IMPRIME PGG.

The binding of the conjugated and unconjugated β-glucans, subsequent staining with BfD IV (U.S. Pat. No. 6,294,321), and flow cytometry were performed as described in Example 1. Results are shown in FIG. 5.

Example 5

Figure 6:
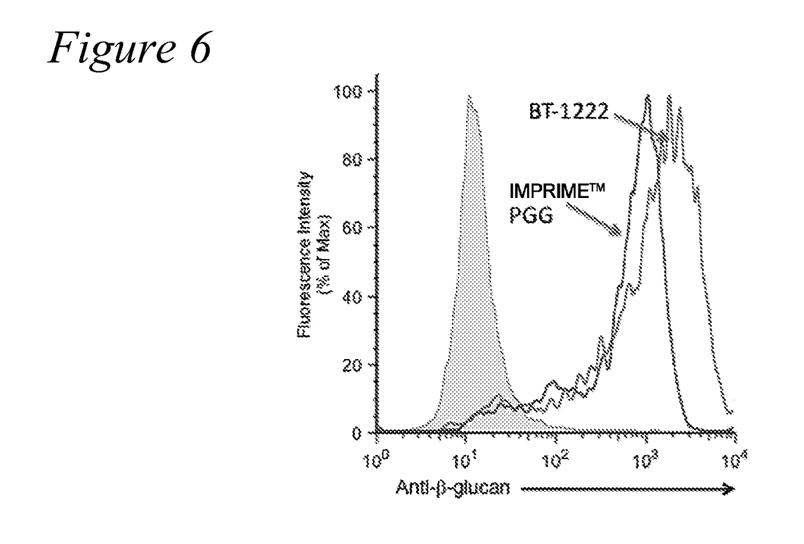
FIG. 6. IMPRIME PGG vs. Benzyl-amine derivatized IMPRIME PGG (BT-1222) binding to human B cells in whole blood.

This example demonstrates that derivatization of IMPRIME PGG enhances its binding capacity to human B cells. The histogram of FIG. 6 shows that the mean fluorescent intensity (MFI) of BfD IV staining on B cells treated with a benzyl amine derivative of IMPRIME PGG (BT-1222) is higher at the tested concentration (10 μg/mL) compared to parent cells treated with underivatized IMPRIME PGG.

Example 6

Whole blood was incubated with 10 μg/mL IMPRIME PGG, ERBITUX (Eli Lilly and Co., New York, N.Y. and Bristol-Myers Squibb Co., Princeton, N.J.), ERBITUX-IMPRIME PGG conjugate, or citrate buffer (as a control) for 30 minutes at 37° C. Cells were washed twice with PBS before staining with the β-glucan specific antibody BfD IV (U.S. Pat. No. 6,294,321). Cells were washed again and stained with an antibodies specific for human IgG to detect ERBITUX and CD19 to label B cells. Cells were analyzed on and LSRII flow cytometer and the groups were compared by gating on CD19⁺ B cells. In the left panel, cells treated with either IMPRIME PGG or the ERBITUX conjugate were positive for β-glucan but only the conjugate treated group had an increase in anti-human IgG binding in the right panel showing the conjugated β-glucan was able to target the CD19⁺ B cell population. Results are shown in FIG. 7.

Example 7

PBMC Staining with 3 μM Fura Red and Fluo-4

FURA RED and FLUO-4 (each from Invitrogen, Life Technologies Corp., Carlsbad, Calif.) calcium stain was added to serum free RPMI medium to a final concentration of 3 μM for each dye, then incubated at 37° C. for 30 minutes. PBMCs mixed 1:1 with media containing 10% FCS and incubated an additional 10 minutes. The cells were washed 2× with media containing 10% FCS. Cells were resuspended in RPMI with 10% human serum.

The resuspended cells were incubated with or without the addition of 100 μg/mL IMPRIME PGG at 37° C. for one hour. The monoclonal antibody CD20 APC (BioLegend, Inc., San Diego, Calif.) was added to each tube for 10 minute incubation before washing 2× with RPMI containing 10% FCS. Cells were resuspended in RPMI with 10% FCS for FACS analysis. Calcium flux was induced by stimulating the B cells with goat anti-human IgM at 2.6 μg/mL. Results are shown in FIG. 8 and demonstrate the ability of IMPRIME PGG-treated B cells to have a larger and more sustained calcium flux, which corresponds to increased B cell responsiveness to antigen challenges and/or B cell receptor stimulation.

Example 8

Blood was drawn from untreated donors (n=15) or donors (n=12) treated with particulate oral β-glucan (U.S. Pat. No. 7,981,447) at dosages ranging from 100 mg/day to 1000 mg/day. PBMCs were isolated from blood using a ficoll gradient.

The isolated PBMCs were treated with 6 μM FURA RED and 3 μM FLUO-4 (each from Invitrogen, Life Technologies Corp., Carlsbad, Calif.) in PBS for 45 minutes at 37° C. The cells were washed 2× with PBS and stained with anti-CD20 APC (BioLegend, Inc., San Diego, Calif.) for 20 minutes at room temperature. Cells were washed 2× and resuspended in RPMI containing 2.5% FCS for FACS analysis. Calcium flux was induced by stimulating the B cells with goat anti-human IgM at 10 μg/mL, 2 μg/mL, or 0.4 μg/mL.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The invention claimed is:

1. A method comprising:
   administering to a subject an amount of a composition effective to bind to B cells and modulate at least one biological function of the B cells, the composition comprising:
   a β-glucan moiety; and
   an active moiety coupled to the β-glucan moiety, the active moiety comprising an immunomodulator, an antibody, a cytotoxic agent, a cytokine, an inhibitor of Bcl-2, a kinase inhibitor, an mTOR inhibitor, a proteosome inhibitor, or an immunosuppressive agent, with the proviso that the active moiety does not include an antigen.

2. The method of claim 1 wherein the β-glucan moiety comprises a soluble β-glucan or a particulate β-glucan.

3. The method of claim 1 wherein the β-glucan moiety comprises a derivatized β-glucan.

4. The method of claim 1 wherein the β-glucan moiety is isolated from yeast.

5. The method of claim 4 wherein the yeast comprises *Saccharomyces cerevisiae*.

6. The method of claim 1 wherein the active moiety comprises an immunomodulator, an antibody, an antigen, a cytotoxic agent, a cytokine, or an immunosuppressive agent.

7. The method of claim 1 wherein the β-glucan moiety and the active moiety are coupled through a covalent linkage.

8. The method of claim 1 wherein the β-glucan moiety and the active moiety are coupled through an affinity linkage.

9. The method of claim 1 wherein at least one biological function of the B cells comprises making an immunoglobulin.

10. The method of claim 1 wherein modulating at least one B cell biological function comprises killing B cells.

11. A β-glucan compound comprising:
    a β-glucan moiety; and
    an active moiety coupled to the β-glucan moiety, the active moiety comprising an immunomodulator, an antibody, a cytotoxic agent, a cytokine, an inhibitor of Bcl-2, a kinase inhibitor, an mTOR inhibitor, a proteosome inhibitor, or an immunosuppressive agent, with the proviso that the active moiety does not include an antigen.

12. A pharmaceutical composition comprising:
    a β-glucan compound comprising:
    a β-glucan moiety; and
    an active moiety coupled to the β-glucan moiety, the active moiety comprising an immunomodulator, an antibody, a cytotoxic agent, a cytokine, an inhibitor of Bcl-2, a kinase inhibitor, an mTOR inhibitor, a proteosome inhibitor, or an immunosuppressive agent, with the proviso that the active moiety does not include an antigen; and
    a pharmaceutically acceptable carrier.

13. The β-glucan compound of claim 11 wherein the active moiety comprises an immunomodulator, an antibody, a cytotoxic agent, a cytokine, or an immunosuppressive agent.

14. The β-glucan moiety of claim 11 wherein the β-glucan moiety is isolated from yeast.

15. The β-glucan moiety of claim 14 wherein the yeast comprises *Saccharomyces cerevisiae*.

16. The β-glucan moiety of claim 11 wherein the β-glucan moiety and the active moiety are coupled through a covalent linkage.

17. The β-glucan moiety of claim 11 wherein the β-glucan moiety and the active moiety are coupled through an affinity linkage.

18. The pharmaceutical composition of claim 12 wherein the active moiety comprises an immunomodulator, an antibody, a cytotoxic agent, a cytokine, or an immunosuppressive agent.

19. The pharmaceutical composition of claim 12 wherein the β-glucan moiety is isolated from yeast.

20. The pharmaceutical composition of claim 19 wherein the yeast comprises *Saccharomyces cerevisiae*.

21. The pharmaceutical composition of claim 12 wherein the β-glucan moiety and the active moiety are coupled through a covalent linkage.

22. The pharmaceutical composition of claim 12 wherein the β-glucan moiety and the active moiety are coupled through an affinity linkage.

* * * * *